United States Patent [19]

Cullum et al.

[11] 3,966,901

[45] June 29, 1976

[54] DENTIFRICE PREPARATION

[75] Inventors: Douglas Charles Cullum, East Molesey; Joan Collinge, Cheadle, both of England

[73] Assignee: Colgate-Palmolive Company, New York, N.Y.

[22] Filed: Feb. 21, 1975

[21] Appl. No.: 551,870

Related U.S. Application Data

[63] Continuation of Ser. No. 389,628, Aug. 21, 1973, abandoned, which is a continuation of Ser. No. 210,559, Dec. 21, 1971, abandoned.

[30] Foreign Application Priority Data

Dec. 29, 1970 United Kingdom............ 61614/70

[52] U.S. Cl................................. 424/52; 424/49; 106/62
[51] Int. Cl.² ............................................. A61K 7/18

[58] Field of Search ............................. 424/49–52

[56] References Cited

UNITED STATES PATENTS

| 3,227,617 | 1/1966 | Manahan et al. ............... 424/52 |
| 3,227,618 | 1/1966 | Manahan et al. ............... 424/52 |
| 3,308,029 | 3/1967 | Saunders ............................ 424/52 |

*Primary Examiner*—Lewis Gotts
*Assistant Examiner*—Cary Owens
*Attorney, Agent, or Firm*—Robert L. Stone; Murray M. Grill; Herbert S. Sylvester

[57] ABSTRACT

The present invention relates to a dentifrice preparation containing a water-soluble monofluorophosphate and a polishing material containing at least a major proportion of dimagnesium orthophosphate.

4 Claims, No Drawings

DENTIFRICE PREPARATION

This is a continuation of application Ser. No. 389,628 filed Aug. 21, 1973 now abandoned which is a continuation of application Ser. No. 210,559, filed Dec. 21, 1971, now abandoned.

The present invention relates to a dentifrice preparation containing a water-soluble monofluorophosphate and a polishing material containing at least a major proportion of dimagnesium orthophosphate.

Water soluble monofluorophosphates and particularly alkali metal monofluorophosphates such as sodium monofluorophosphate have been disclosed and used as fluorine-providing active ingredients in dentifrice preparations. The polishing agents which may be used for such dentifrices have been the subject of much investigation.

A dentifrice containing sodium monofluorophosphate and a polishing agent which is principally dicalcium orthophosphate is known to be highly effective in reducing the formation of caries. This dentifrice does tend to lose a portion of its effectiveness when subject to prolonged aging. It has therefore been most desirable to use it in relatively fresh condition.

It is an advantage of this invention that a dental cream is obtained which provides fluorine and is highly stable upon prolonged aging. Other advantages will be apparent from consideration of the following specification.

In accordance with certain of its aspects, this invention relates to a dentifrice preparation which comprises a water-soluble monofluorophosphate and compatible polishing material at least a major part of which is dimagnesium orthophosphate.

The water-soluble monofluorophosphate is preferably sodium monofluorophosphate. Sodium monofluorophosphate ($Na_2PO_3F$) is a water-soluble material which releases monofluorophosphate ions in water, and it may be mixed with the polishing material in any suitable amount. Such dental preparation is compatible with suitable amounts of surface-active agents, gum, etc., as described. The sodium monofluorophosphate as commercially available may vary considerably in purity. It may be used in any suitable purity provided that any impurities do not substantially adversely affect the desired properties. In general, the purity is desirably at least about 80%. For best results, it should be at least 85%, and preferably at least 90% by weight of sodium monofluorophosphate with the balance being primarily impurities or by-products of manufacture such as sodium fluoride, water-soluble sodium phosphate salt, and the like. Expressed in another way, the sodium monofluorophosphate employed should have a total fluoride content of about 12%, preferably above 12.7%; a content of not more than 1.5%, preferably not more than 1.2% of free sodium fluoride; and a sodium monofluorophosphate content of at least 12%, preferably at least 12.1%, all calculated as fluorine.

In addition to sodium monofluorophosphate, other monofluorophosphate salts which have sufficient water solubility for use in the instant invention include calcium monofluorophosphate, magnesium monofluorophosphate and aluminum monofluorophosphate. The term "monofluorophosphate" also includes monofluoropolyphosphates such as $Na_4P_3O_9F$, $K_4P_3O_9F$, $(NH_4)_4P_3O_9F$, $Na_3 KP_3O_9F$, $(NH_4)_3NaP_3O_9F$ and $Li_4P_3O_9F$.

The amount of monoflurophosphate in the dentifrice may be varied but should be an effective, non-toxic amount providing about 0.01–1% by weight of fluorine to the dentifrice. Thus, sodium monofluorophosphate is typically used in amounts of about 0.05–7.6% by weight. It is preferred that the sodium monofluorophosphate salt be no more than about 2%, and usually within the range of about 0.05% to about 1%, by weight of the dentifrice.

The polishing material contains at least a major proportion of dimagnesium orthophosphate, preferably dimagnesium orthophosphate trihydrate. Other suitable dimagnesium orthophosphates may be used, including the heptahydrate. The dimagnesium orthophosphate may be used singly as the sole polishing agent. If desired, it may also be used in combination with other polishing agents as the major ingredient (more than 50% by weight) of the polishing material. A single form of the dimagnesium orthophosphate may be used as well as mixtures of the hydrates in any suitable ratio resulting from a blend or formed in situ in the manufacture of the dimagnesium orthophosphate. Such an additional polishing agent includes calcium carbonate such as natural chalk and precipitated calcium carbonate in minor proportion (i.e. less than 50% by weight) of the polishing material. Magnesium carbonate may also be used as a minor component of the polishing material, instead of or in addition to calcium carbonate. These polishing materials are employed in finely powdered form of any suitable particle size for effective polishing power.

In the case of the dimagnesium orthophosphate and alkaline earth metal carbonate (such as calcium carbonate and/or magnesium carbonate) mixtures, the ratio of these materials is variable and is preferably in the range of about 99:1 to about 65:35 by weight, and usually about 25:1 to 3:1, depending upon the particular form of orthophosphate and the particular carbonate used. In general, it is preferred to prepare dental creams having 35–60% polishing material with dimagnesium orthophosphate as the main polishing ingredient and from 0 to 15% calcium carbonate or magnesium carbonate in the dental cream. If desired other polishing materials may be added in suitable amount such as hydrated alumina, calcium pyrophosphate, tricalcium phosphate, calcium polymetaphosphate and the like. The total content of polishing agents will be usually at least 20%, such as about 20–99% and particularly from 20–75%, preferably 35–60%, in toothpastes and at least 70% in tooth powders.

Any suitable surface active or detersive material may be included in the dentifrice compositions. Such compatible materials are desirable to provide additional detersive, foaming and anti-bacterial properties depending upon the specific type of surface active material and are selected similarly. These detergents are water-soluble organic compounds usually, and may be anionic, non-ionic or cationic in structure. It is preferred to use the water-soluble salts of higher fatty acid monoglyceride monosulphate detergent (e.g. sodium coconut fatty acid monoglyceride monosulphate), higher alkyl sulphate (e.g. sodium lauryl sulfate), alkyl aryl sulphonate (e.g. sodium dodecyl benzene sulphonate) higher fatty acid esters of 1,2-dihydroxy propane sulphonate (e.g. sodium coconut fatty acid ester of 1,2-dihydroxy propane sulphonate), and the like.

In various surface active materials may be used in any suitable amount, generally from about 0.05 to about 10% by weight, and preferably from about 0.5 to 5% by weight of the dentifrice composition.

It is a further embodiment of the present invention to use the substantially saturated higher aliphatic acyl amides of lower aliphatic amino carboxylic acid compounds, such as those having 12 to 16 carbons in the acyl radical, and as more particularly described in U.S. Pat. No. 2,689,170, issued Sept. 14, 1954. The amino acid portion is derived generally from the lower aliphatic saturated monoaminocarboxylic acids having about 2 to 6 carbons, usually the monocarboxylic acid compounds. Suitable compounds are the fatty acid amides of glycine, sarcosine, alanine, 3-amino propanoic acid and valine having about 12 to 16 carbons in the acyl group. It is preferred to use the N-lauroyl, myristoyl and palmitoyl sarcoside compounds however for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl myristoyl and palmitoyl, ammonium and ethanolamine N-lauroyl sarcosides and N-lauroyl sarcosine, and sodium N-lauroyl glycide and alanide. For convenience herein, reference to "amino carboxylic acid compound," "sarcoside," and the like refers to such compounds having a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such fatty acid material is less than 15% by weight of the amide and insufficient to substantially adversely affect it, and preferably less than about 10% of said amide material.

In accordance with the present invention, the specified combinations of ingredients may be used in any suitable preparation designed for application to the oral cavity which preparation is referred to herein as a dentifrice preparation. Such dentifrices may be in solid, liquid or paste form and include tooth pastes or dental creams, tooth powders, liquid dentifrices, tablets and the like. Such products are prepared in the usual manner. In the preparation of tooth powders, it is usually sufficient to mechanically admix the various solid ingredients.

In dental cream formulations, the liquids and solids should necessarily be proportioned to form a creamy mass of desired consistency which is extrudible from a collapsible aluminium or lead tube for example. In general, the liquids in the dental cream will comprise chiefly water, glycerine, sorbitol, propylene glycol, or the like, including suitable mixtures thereof. It is advantageous usually to use a mixture of both water, and a humectant or binder such as glycerine, sorbitol or mixtures thereof. The total liquid content will generally be about 20–75% by weight of the formulation. It is preferred to use also a gelling agent in dental creams such as the natural and synthetic gums and gum-like materials, e.g. Irish Moss, gum tragacanth, sodium carboxymethylcellulose, polyvinylpyrrolidone, starch and the like. The Irish Moss and sodium carboxymethylcellulose, are compatible particularly and are preferred gelling agents. The gum content is usually in an amount up to about 10% and preferably about 0.5–5% by weight of the formulation.

Other types of dentifrice compositions will be formulated in known manner also.

A minor amount of hydrated aluminium oxide may be incorporated in the dentifrice preparation. More particularly, a dental cream having improved physical properties may be prepared from a mixture of the dimagnesium orthophosphate trihydrate optionally with a minor amount of calcium carbonate or magnesium carbonate or dimagnesium orthophosphate heptahydrate suspended in a gel comprising water, humectant and gelling agent, with said monofluorophosphate compound and organic non-soap synthetic detergent, and preferably a minor amount of hydrated aluminium oxide. These dental creams exhibit a superior degree of cosmetic properties and physical stability to aging for long periods of time. The aluminium oxide acts as a stabilizing and modifying agent so as to eliminate or inhibit any tendency for separation or "bleeding" of the dental cream in the collapsible tube.

Suitable examples of hydrated aluminium oxide which may be employed are the forms known as alpha and beta aluminium oxide trihydrate and mixtures thereof. It is used usually in the form of fine particles of any desired particle size in the manufacture of the dental cream. In practice, it is preferred to use the alpha trihydrate form of which at least about 90% of the particles pass through on a U.S. standard No. 325 mesh sieve and not more than about 5% of the particles by weight are less than 5 microns. It has been found that amounts of hydrated aluminium oxide and from about ¼ to about 10% by weight are most desirable.

The dentifrices may have any pH practicable for use. If necessary, acidifying agents or basic materials may be added to adjust the pH as desired. For example, a suitable acidifying agent such as citric acid or other weak organic acid may be employed in varying amount if necessary to adjust the pH of the dental cream.

There may be employed also various calcium and magnesium ion suppression agents for adjustment of physical properties of the compositions. Suitable agents are the water-soluble inorganic polyphosphate salts, such as tetrasodium pyrophosphate or disodium diacid pyrophosphate, with the partially neutralized or acid polyphosphates preferred. Other suitable agents are the alkali metal, preferably sodium, salts of citric acid. In general, such compounds will be a minor amount or proportion of the formulation. The precise amount will vary depending upon the specific formulation, such as the physical characteristics of the dental cream, but will usually be from about 0.1% to about 3% by weight.

Various other materials may be incorporated in the dentifrice preparations of this invention. Examples thereof are colouring or whitening agents or dyestuffs, preservatives, silicones, chlorophyll compounds, ammoniated materials such as urea, diammoniumphosphate and mixtures thereof, and other constituents. The adjuvants are incorporated in the instant compositions in amounts which do not substantially adversely affect the properties and characteristics desired and are selected and used in proper amounts depending upon the particular type of preparation involved.

Antibacterial agents may also be employed in the oral preparations of the instant invention in amount of about 0.01–5% by weight. Typical antibacterial agents include $N^1$-(4-chlorobenzyl)-$N^5$-(2,4-dichlorobenzyl) biguanide;

p-chlorophenyl biguanide;

4-chlorobenzhydryl biguanide;
4-chlorobenzhydrylguanylurea;
N-3-lauroxylpropyl-N⁵-p-Chlorobenzylbiguanide;
1,6-di-p-chlorophenylbiguanidohexane;
1-(lauryldimethylammonium)-8-(p-chlorobenzyl-dimethylammonium) octane dichloride;
5,6-dichloro-2-guanidinobenzimidazole;
N¹-p-chlorophenyl-N⁵-laurylbiguanide;
5-amino-1,3-bis(2-ethylhexyl)-5-methylhexahydro pyrimidine;
and their non-toxic acid addition salts.

The following specific example is further illustrative of the nature of the present invention, but is to be understood that the invention is not limited thereto. The compositions are prepared in the usual manner and all amounts of the various ingredients are by weight unless otherwise specified.

EXAMPLE

The following dental creams are parepared:

| INGREDIENTS | PARTS | | | |
|---|---|---|---|---|
| | A. | B. | C. | D. |
| Sodium monofluorophosphate | 0.76 | 0.76 | 0.76 | 0.76 |
| Sodium N-lauroyl sarcosinate | 2.00 | 2.00 | 2.00 | 2.00 |
| Dimagnesium orthophosphate trihydrate | 43.76 | 38.76 | 40.00 | 40.00 |
| Calcium carbonate | 5.00 | 5.00 | — | — |
| Glycerine | 22.00 | 22.00 | 10.00 | — |
| Sorbitol (70%) | — | — | 12.00 | 22.00 |
| Sodium carboxymethyl cellulose | 0.85 | 0.90 | 0.90 | 0.95 |
| Water (with very small amounts of sodium saccharin, preservative, flavor, color as desired) | Q.S. to | Q.S. to | Q.S. to | Q.S. to |
| | 100 | 100 | 100 | 100 |

These dental creams have superior qualities and retain high levels of fluorine during prolonged storage. Calcium carbonate in formulations A and B may be replaced in whole or in part by magnesium carbonate to form satisfactory stable dental creams also.

It will be apparent to those skilled in the art that various modifications of the above Example can be made thereto.

We claim:

1. A dental cream preparation comprising a water-soluble alkali metal monofluorophosphate in amount to provide about 0.01–1% by weight of fluorine and about 20–99% by weight of compatible polishing material at least a major part of which is dimagnesium orthophosphate trihydrate.

2. The preparation claimed in claim 1 wherein said monofluorophosphate is sodium monofluorophosphate which is present in amount of about 0.05–7.6% by weight.

3. The dental cream preparation claimed in claim 1 wherein said preparation is in a collapsible aluminum tube.

4. The dental cream preparation claimed in claim 1 wherein said polishing material consists essentially of dimagnesium orthophosphate trihydrate and a carbonate selected from the group consisting of calcium carbonate and magnesium carbonate, the ratio of said dimagnesium orthophosphate trihydrate to said carbonate being in the range of about 99:1 to about 65:35 by weight.

* * * * *